(12) United States Patent
Blanck et al.

(10) Patent No.: US 11,446,082 B2
(45) Date of Patent: Sep. 20, 2022

(54) ELECTRONIC SWITCHBOX

(71) Applicant: St. Jude Medical, Cardiology Division, Inc., St. Paul, MN (US)

(72) Inventors: Arthur Gerald Blanck, Ramona, CA (US); Michael C. Bednarek, Buffalo, MN (US); Sebastian Teodoru, Irvine, CA (US)

(73) Assignee: St. Jude Medical Cardiology Division, Inc., St. Paul, MN (US)

( * ) Notice: Subject to any disclaimer, the term of this patent is extended or adjusted under 35 U.S.C. 154(b) by 929 days.

(21) Appl. No.: 15/878,522

(22) Filed: Jan. 24, 2018

(65) Prior Publication Data
US 2018/0221085 A1     Aug. 9, 2018

Related U.S. Application Data

(60) Provisional application No. 62/454,345, filed on Feb. 3, 2017.

(51) Int. Cl.
*A61B 18/14* (2006.01)
*A61B 18/12* (2006.01)
(Continued)

(52) U.S. Cl.
CPC .......... *A61B 18/1492* (2013.01); *A61B 5/287* (2021.01); *A61B 5/4836* (2013.01); *A61B 18/1206* (2013.01); *A61N 1/3956* (2013.01); *A61B 2018/0094* (2013.01); *A61B 2018/00351* (2013.01); *A61B 2018/00577* (2013.01); *A61B 2018/00613* (2013.01); *A61B 2018/00642* (2013.01); *A61B 2018/00839* (2013.01); *A61B 2018/1266* (2013.01); *A61B 2018/1293* (2013.01); *A61B 2560/0219* (2013.01); *A61B 2562/166* (2013.01); *A61N 1/3962* (2013.01);
(Continued)

(58) Field of Classification Search
CPC .. A61B 5/24; A61B 5/287; A61B 5/30; A61B 5/304; A61B 5/308; A61B 5/318; A61B 5/4836; A61B 5/6846; A61B 5/6852; A61B 2018/00351; A61B 2018/00577; A61B 2018/00613; A61B 2018/00839; A61B 2018/1266; A61B 2018/1293; A61B 18/1492; A61N 1/0563; A61N 1/3956; A61N 1/3962; A61N 1/3987
See application file for complete search history.

(56) References Cited

U.S. PATENT DOCUMENTS

| | | | | |
|---|---|---|---|---|
| 5,357,956 | A * | 10/1994 | Nardella | A61B 5/0538 600/374 |
| 6,438,419 | B1 * | 8/2002 | Callaway | A61N 1/3925 600/508 |

(Continued)

FOREIGN PATENT DOCUMENTS

| | | |
|---|---|---|
| WO | 9410904 A1 | 5/1994 |
| WO | 2005112809 A2 | 12/2005 |

*Primary Examiner* — Ronald Hupczey, Jr.
*Assistant Examiner* — Bradford C. Blaise
(74) *Attorney, Agent, or Firm* — Armstrong Teasdale LLP (57) ABSTRACT

Aspects of the present disclosure are directed to an electronic switchbox for automatically switching between receive and transmit functionalities. In one embodiment, an electronic switchbox automatically switches between receiving electrocardiograph signals and transmitting cardioversion impulses.

16 Claims, 6 Drawing Sheets

(51) Int. Cl.
*A61N 1/39* (2006.01)
*A61B 5/00* (2006.01)
*A61B 5/287* (2021.01)
*A61B 18/00* (2006.01)
*H03K 17/687* (2006.01)

(52) U.S. Cl.
CPC ........ *A61N 1/3987* (2013.01); *H03K 17/6871* (2013.01)

(56) References Cited

U.S. PATENT DOCUMENTS

| | | | |
|---|---|---|---|
| 2003/0036774 A1* | 2/2003 | Maier | A61N 1/3918 607/5 |
| 2003/0125770 A1* | 7/2003 | Fuimaono | A61N 1/0563 607/5 |
| 2004/0049117 A1* | 3/2004 | Ideker | A61N 1/3925 600/510 |
| 2004/0054383 A1 | 3/2004 | Ryan et al. | |
| 2005/0256521 A1* | 11/2005 | Kozel | A61B 5/6858 606/41 |
| 2010/0023004 A1* | 1/2010 | Francischelli | A61B 18/1442 606/41 |
| 2011/0319948 A1 | 12/2011 | Onodera et al. | |
| 2013/0338520 A1* | 12/2013 | Govari | A61B 5/7217 600/522 |
| 2014/0005664 A1* | 1/2014 | Govari | A61B 18/1492 606/41 |

\* cited by examiner

ELECTRONIC SWITCHBOX

CROSS-REFERENCE TO RELATED APPLICATIONS

This application claims the benefit of U.S. Provisional Application No. 62/454,345, filed 3 Feb. 2017, the entire disclosure of which is incorporated by reference herein in its entirety.

BACKGROUND a. Field

The instant disclosure relates to an electronic switchbox for automatically switching between receive and transmit functionalities. In one embodiment, the instant disclosure relates to an electronic switchbox that automatically switches between receiving electrocardiograph signals and transmitting cardioversion impulses.

b. Background Art

In cardiovascular cardioversion and irreversible electroporation therapies, electrodes at a distal end of a cardiovascular catheter may be utilized to both conduct a therapy and provide electrophysiological diagnostic information to the clinician. For example, the electrodes at the distal end of the catheter may provide diagnostic data by way of electrocardiograph signals (also referred to as ECG signals), and ablation therapy on myocardial tissue of a cardiac muscle via either cardioversion or electroporation ablation therapies. Ablation therapies are commonly used to necrose myocardial tissue in a cardiac muscle, which may alleviate symptoms associated with epicardial ventricular tachycardia, atrial fibrillation, and other cardiac conditions.

Manual electronic switchboxes, which allow for dual use of electrodes at a distal tip of a catheter, require a clinician to manually switch between cardioversion or irreversible electroporation transmit and ECG receive modes. However, such manual electronic switchboxes prevent the clinician from receiving ECG signals immediately following a cardioversion or electroporation therapy, as the clinician is unable to manually switch the electronic switchbox in such a short period of time.

The foregoing discussion is intended only to illustrate the present field and should not be taken as a disavowal of claim scope.

BRIEF SUMMARY

Aspects of the present disclosure relate to an electronic switchbox for automatically switching between receive and transmit functionalities. In one embodiment, the instant disclosure relates to an electronic switchbox that automatically switches between receiving electrocardiograph signals and transmitting cardioversion impulses.

Embodiments of the present disclosure are directed to electronic switchboxes that include impulse detection circuitry and a switch matrix with one or more switches. The impulse detection circuitry detects a pulse emitted from a signal generator, and the switch matrix operates in one of two modes. In the first mode, the pulse is electrically isolated from an electrocardiograph monitor and a plurality of catheter electrodes. In response to an activation signal from the impulse detection circuitry indicative of the pulse, the switch matrix operates in a second mode. In the second mode, the pulse is electrically coupled to at least one of the catheter electrodes, and a high impedance state protects the electrocardiograph monitor from the cardioversion pulse. In more specific/detailed embodiments, the electronic switchbox further includes charge collector circuitry electrically coupled between driver circuitry and the impulse detection circuitry. The charge collector circuitry stores energy from the cardioversion pulse and powers the driver circuitry during the pulse.

Various embodiments of the present disclosure are directed to a cardiovascular catheter system. The cardiovascular catheter system including a signal generator, an electrocardiograph monitor, a cardiac catheter, and an electronic switchbox including impulse detection circuitry and a switch matrix. The signal generator generates an electrical pulse for cardioverting or ablating tissue. The electrocardiograph monitor receives and monitors electrocardiograph signals indicative of the electrical activity of a heart. The cardiac catheter includes a plurality of electrodes along a length of a distal portion, the electrodes electrically coupled to tissue, and cardioverts or ablates the tissue in response to the electrical pulse. The impulse detection circuitry is electrically coupled to the signal generator, and detects the electrical pulse emitted from the signal generator. The switch matrix includes one or more switches, an input port, and an output port. The switch matrix is electrically coupled to the impulse detection circuitry and the signal generator at the input port, and the plurality of electrodes and the electrocardiograph monitor at the output port. The switch matrix operates in first and second modes. In the first mode, the electrical pulse is isolated from the electrocardiograph monitor and the catheter electrodes. In the second mode, in response to an activation signal from the impulse detection circuitry indicative of the electrical pulse, the electrical pulse is communicated to at least one of the catheter electrodes, and a high impedance state protects the electrocardiograph monitor from the electrical pulse. In more detailed embodiments, the electronic switch box further includes driver circuitry. The driver circuitry changes the switch matrix between the first and second modes in response to a trigger signal from the impulse detection circuitry. In such an embodiment, the impulse detection circuitry uses the energy from the electrical pulse to deliver the trigger signal to the driver circuitry.

Yet other embodiments of the present disclosure are directed toward methods of operating an electronic switch box. The method includes operating in first and second modes. In the absence of an electrical pulse, the switchbox operates in the first mode, whereby an input port of the switch box is isolated from an electrocardiograph monitor and a plurality of catheter electrodes are electrically coupled to an output port of the switch box. The switchbox operates in the second mode, in response to the electrical pulse. In the second mode, the input port that receives the electrical pulse is electrically coupled to at least one of the catheter electrodes, and the electrocardiograph monitor via the output port of the switch box. The electrocardiograph monitor is protected from the electrical pulse by a high impedance between the output port of the switch box and the electrocardiograph monitor. In more specific implementations, electrocardiograph signals from the catheter electrodes are communicatively coupled to the electrocardiograph monitor during both the first and second modes.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Aspects of the present disclosure are directed to an electronic switchbox for automatically switching between a receive and transmit functionality. In one embodiment, the instant disclosure relates to an electronic switchbox that automatically switches between receiving electrocardiograph signals and transmitting cardioversion impulses. Yet other embodiments of the present disclosure are directed to switching between receiving electrocardiograph signals and transmitting direct current, irreversible electroporation impulses. While various embodiments of the present disclosure are described in relation to cardiac applications, such embodiments are provided for exemplary purposes and are not intended to limit the scope of the present disclosure.

Aspects of the present disclosure are directed to both powered and unpowered electronic switchboxes. In unpowered implementations, the switchbox includes electrical circuitry that detects a defibrillator impulse signal, charges the switchbox from the defibrillator impulse signal, and activates a switch matrix. In many embodiments, the switch matrix executes a switch between cardioversion and ECG recording signals. As a result, a clinician may see ECG signals on an ECG monitor immediately before and after the cardioversion without any manual switching. In powered implementations of the present disclosure, the switchbox may include electrical circuitry that detects a defibrillator impulse signal, charges the switchbox from a dedicated power source and activates the switch matrix without drawing on the defibrillator impulse signal to power the switch matrix.

In specific embodiments of the present disclosure, an unpowered switchbox may be used in conjunction with various band electrode configurations where ECG signals and cardioversions signals are needed for both diagnostic and cardioversion purposes, respectively. Due to the power demands of the switchbox, a percentage of the energy of a cardioversion signal will be used to activate an electronic switch that will allow switching between cardioversion and ECG signals. The impulse signal may be between 5 joules ("J") to 30 J, with 30 J being maximum power for some applications. Peak current of a leading edge of the cardioversion signal will be reduced due to the energy consumption necessary to activate the switchbox.

Unpowered switchboxes in accordance with the present disclosure may include impulse detection circuitry and a switch matrix. The impulse detection circuitry detects the defibrillation pulse, controls the power drawn from the defibrillator impulse signal, and provides an activation signal to the switch matrix. In response to the activation signal from the impulse detection circuitry, the switch matrix switches between coupling catheter electrodes with defibrillation circuitry and electrocardiograph recording circuitry (also referred to as an ECG monitor). Specifically, the switch matrix connects the patient to the defibrillator in cardioversion mode when the defibrillator is activated and the switch matrix is powered, and connects the patient to an ECG Recording system when the defibrillator signal is extinguished and the switch matrix is powered-off.

Of particular concern, in various embodiments of an unpowered switch matrix, is minimizing the delay between a defibrillator impulse and the switch box energizing and switching its state. Where the switch box takes an excessive amount of time to power-up and change state, a leading edge of the defibrillation impulse may be cut off and never delivered to a patient. Further, the energy draw of the switch matrix may also degrade the efficacy of the therapy where the switch matrix draws an excessive amount of power from the defibrillator impulse to maintain the switch matrix in the desired state. Aspects of the present disclosure are directed toward minimizing both the switch matrix delay time, and in unpowered switch matrix embodiments—the power draw of the switch matrix.

In some powered switchbox implementations, impulse detection circuitry includes an independent power source. In such embodiments, the switch matrix may be replaced with a fast relay-switch, provided that the delay in restoring ECG signals after a defibrillation impulse is acceptable for the desired application.

Details of various embodiments of the present disclosure are described below with specific reference to the figures.

Figure 1:
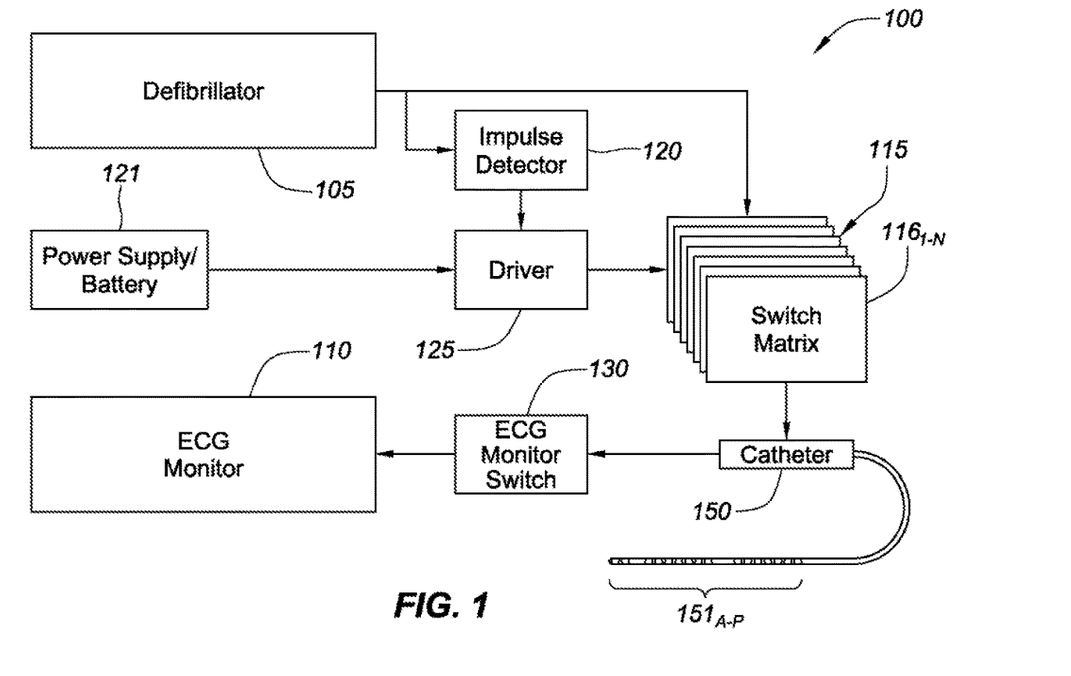
FIG. 1 is a block diagram of a catheter system including a powered electronic switchbox, consistent with various aspects of the present disclosure.

FIG. 1 is a block diagram of a catheter system 100 including a powered electronic switch matrix 115, consistent with various aspects of the present disclosure. Upon activation of defibrillator 105, a defibrillation pulse is applied to the impulse detector 120 and the switch matrix 115 including at least one of a plurality of switches 116$_{1-N}$. The impulse detector circuitry 120 detects the defibrillation pulse and uses energy from the defibrillation pulse to trigger driver circuitry 125 for the entirety of a monophasic or bi-phasic waveform of the defibrillation pulse. Power Supply/Battery 121 provides the necessary energy to power the driver circuitry 125, which triggers the switch matrix 115 in response to an activation signal from the impulse detector 120. The switch matrix 115 is in a normally open or high impedance state. When activated by the driver circuitry 125, the switch matrix 115 is driven into a closed or low impedance state which directs the defibrillation pulse to the catheter 150. An ECG Monitor Switch 130 is normally in a low impedance state and directs the various ECG waveforms from the catheter 150 to ECG monitor 110. Upon detection of the high energy defibrillation pulse, the ECG monitor switch 130 switches into a high impedance state, which reduces the energy from the defibrillation pulse delivered to the ECG monitor 110, allowing for (near) continuous patient monitoring during the defibrillation procedure, while protecting the ECG monitor 110 from damage associated with the defibrillation pulse.

By implementing a catheter system 100 as described in reference to FIG. 1, the complexity of the catheter 150 may be greatly reduced. For example, the number of lead wires extending through the catheter 150 may be reduced as the same lead wires may be used for both transmitting defibrillation pulses and receiving ECG signals from electrodes 151$_{A-P}$. Furthermore, the number of electrodes 151$_{A-P}$ necessary to provide the desired therapy and diagnostic capabilities is also reduced. This catheter complexity reduction may all be accomplished while increasing the functionality of the catheter system 100—allowing for (near) continuous patient monitoring during the defibrillation procedure.

In various embodiments of the present disclosure, switch matrix 115 includes a plurality of switches 116$_{1-N}$. The plurality of switches allows for a number of variations of catheter system 100 functionality. For example, where it is not necessary to receive ECG signals during the defibrillation procedure (also referred to as cardioversion), the switch matrix 115 may use switch 116$_1$ to electrically decouple the ECG monitor 110 from one or more of electrodes 151$_{A-P}$, while switch 116$_2$ electrically couples one or more electrodes 151$_{A-P}$ to defibrillator 105 for delivering a defibrillator impulse to tissue in contact with the electrodes 151. In such an embodiment, the ECG monitor switch 130 is not necessary as the ECG monitor 110 is already isolated from the defibrillator impulse by the switch matrix 115.

Some embodiments of the present disclosure are directed toward minimizing a time delay between detecting a defibrillation pulse and activating the switch matrix 115. In such an embodiment, instead of relying on the impulse detector circuitry 120 to collect sufficient energy from the defibrillation pulse to trigger the driver, the impulse detector circuitry 120 is powered by power supply 121 to mitigate related charge time. Moreover, this prevents the distortion of the front-end of the defibrillation pulse associated with the charge pulled by the impulse detector circuitry 120 to both trigger and power the driver circuitry 125. This is advantageous in precision applications where it is desirable to know the actual power delivered to the electrodes 151$_{A-P}$ by the defibrillation pulse, for example. Importantly, where the impulse detector circuitry 120 uses energy from the defibrillation pulse, the total energy delivered to tissue in contact with the electrodes 151 may be less then intended and negate the efficacy of a cardioversion therapy. However, this may be alternatively solved, in an unpowered configuration, by compensating for the anticipated draw of the impulse detector 120 in the generated defibrillation pulse of the defibrillator 105. In specific embodiments, the defibrillator 105 may compensate for the impulse detector circuitry 120 drawing from the defibrillation pulse by measuring the defibrillation pulse in real-time, after the impulse detector circuitry 120, and extending the length of the pulse to deliver a desired energy to the electrodes 151. In yet other embodiments, the catheter system 100 may maintain a running average of the draw of the impulse detector 120, and compensate for the draw in each defibrillation pulse based on the running average from previous pulses (or just the last pulse).

In various embodiments of the present disclosure, ECG monitor switch 130 may either be powered or unpowered. In the embodiment shown in FIG. 1, the ECG monitor switch 130 is unpowered and relies upon the high energy defibrillation pulse to power the activation of ECG monitor switch 130 into a high impedance state, which protects the ECG monitor 110 from damage associated with the defibrillation pulse. However, as discussed above, drawing energy from the defibrillation pulse also impacts the total amount of energy that is delivered to the tissue during the cardioversion therapy. Accordingly, some embodiments consistent with the present disclosure may also rely upon power supply 121 to power the ECG monitor switch 130, and thereby maintain the defibrillation pulse as generated by the defibrillator 105.

While the ECG monitor switch 130 of FIG. 1 may be independently operable from switch matrix 115, and its plurality of switches 116$_{1-N}$ (as shown in FIG. 1); alternatively, the ECG monitor switch may be integrated with the switch matrix 115. In such an embodiment, a first switch 116$_1$ may be driven into a closed or low impedance state which directs the defibrillation pulse to the catheter 150 by driver circuitry 125. The driver circuitry 125 may also simultaneously drive a second switch 116$_2$ into a high impedance state, which reduces the energy to the ECG monitor 110, and allows for (near) continuous patient monitoring during the defibrillation procedure, while protecting the ECG monitor 110 from damage associated with the defibrillation pulse. Once the driver circuitry 125 is no longer being driven by the impulse detector circuitry 120, the first switch 116$_1$ returns to a high impedance state, and the second switch 116$_2$ returns to a low impedance state—allowing for the ECG monitor 110 to receive ECG signals while the defibrillator is electrically disconnected from catheter 150.

Various embodiments of FIG. 1, where power supply 121 is a battery, prevent damage to the ECG monitor 110 associated with a low battery condition preventing switch matrix 115 from responding to a defibrillation pulse from the defibrillator 105. In one example embodiment, the switch matrix 115 may include at least a first switch 116$_1$ that when unpowered by driver 125 remains in a normally open or high impedance state—where the defibrillator 105 is electrically decoupled from the catheter 150. Such a configuration prevents a defibrillation pulse from reaching the ECG monitor 110 when a power supply 121 is unable to provide the required power to the driver circuitry 125 to activate the switch matrix 115. As discussed above, a defibrillation pulse may damage the ECG monitor 110, rendering it incapable of monitoring the ECG signals received by electrodes 151.

In various embodiments of FIG. 1, electrodes 151$_{A-P}$ may be divided-up and dedicated to either diagnostics (e.g., ECG monitoring) or therapy (e.g., cardioversion). In such an embodiment, though the circuitry for diagnostics and therapy may be isolated from one another, during cardioversion the defibrillation impulse may be of sufficient energy to cause an arc across dedicated electrodes 151. If an arc from a therapy electrode (e.g., 151$_A$) conducts to a diagnostic electrode (e.g., 151$_B$), the power delivered to the ECG monitor 110 may cause damage to the monitor. Accordingly, in such embodiments, the catheter system 100 may still include an ECG monitor switch 130 that isolates the dedicated diagnostic electrode(s) from the ECG monitor 110 during a therapy or provides a high impedance along the diagnostic line in response to a high power defibrillation impulse.

In some specific embodiments, a switch matrix 115 may include a plurality of switches $116_{1-N}$ that enable individual, paired, sectional, even/odd, or other types of addressability of the electrodes $151_{A-P}$. In such an embodiment, the clinician may statically locate a distal portion of catheter 250 (including the electrodes) in contact with a length of a pulmonary vein, or manipulate the distal portion into a loop which contacts a circumferential surface of the pulmonary vein. The clinician may then individually address and conduct diagnostics to portions of tissue along a catheter length, and implement therapies for each of such portions based on the individual diagnostic data for that portion. In such an embodiment, the switch matrix 115 would vary in location from the block diagram shown in FIG. 1, and would also regulate signal travel between the electrodes 151 and ECG monitor 110, allowing for the reception of ECG signals only from selected electrodes. Though such an embodiment would require several additional switch layers in the switch matrix 115, the resulting control would allow for granular control of both diagnostics and therapies along the catheter shaft 150. As one specific example, the catheter system 100 may allow for simultaneous diagnostic and therapeutic procedures. In such an embodiment, the switch matrix 115 may electrically couple one or more intermediary electrodes (e.g., $151_F$) along the catheter 150 with the defibrillator 105 to deliver a defibrillation pulse to tissue in contact with the intermediary electrodes, while one or more electrodes on either side of the intermediary electrodes (e.g., $151_A$ and $151_P$) may be electrically coupled to the ECG monitor by the switch matrix 115 to facilitate real-time diagnostic monitoring of the cardioversion procedure. In such embodiments, the ECG monitor may override the length of the cardioversion therapy where the ECG signals received by the monitor 110 indicate that the tissue in contact with the intermediary electrodes have been sufficiently ablated.

Figure 2:
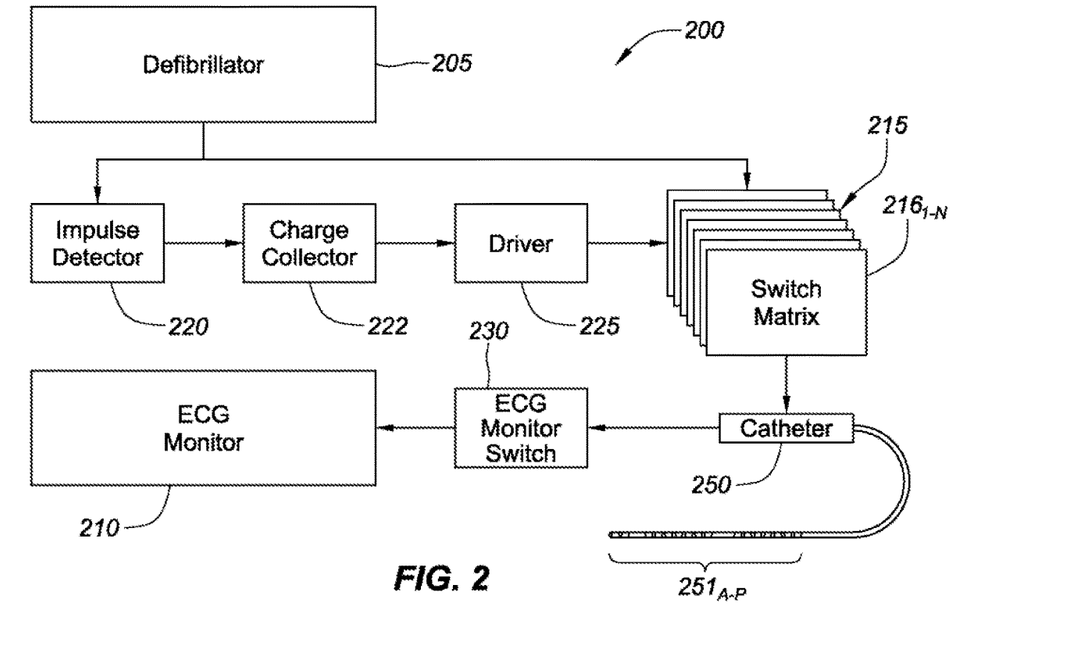
FIG. 2 is a block diagram of a catheter system including an unpowered electronic switchbox, consistent with various aspects of the present disclosure.

FIG. 2 is a block diagram of a catheter system 200 including an unpowered electronic switch matrix 215, consistent with various aspects of the present disclosure. The defibrillator 205, upon activation, delivers a defibrillation pulse to the impulse detector circuitry 220 and one of the switches 216 of the switch matrix 215. The impulse detector circuitry 220 detects the defibrillation pulse and uses energy from the defibrillation pulse to power the charge collector circuitry 222. The charge collector circuitry 222 stores energy from the defibrillation pulse, which has been redirected via the impulse detector 220, for powering driver circuitry 225 for the entirety of a monophasic or bi-phasic waveform of the defibrillation pulse. The driver circuitry 225 regulates the stored energy from the charge collector circuitry 222 and provides the necessary drive voltage to activate the switch matrix 215 for the duration of the defibrillation pulse, after which the switch matrix returns to its normally open or high impedance state. When activated by the driver circuitry 225, the switch $216_N$ is driven into a closed or low impedance state which directs the defibrillation pulse to electrodes 251 of catheter 250. ECG monitor switch 230 is normally in a low impedance state and directs the various ECG waveforms from the catheter to the ECG monitor. Upon detection of a high energy defibrillation pulse, the ECG monitor switch 230 switches into a high impedance state, which reduces the energy to the ECG monitor 210, allowing for continuous patient monitoring during the defibrillation procedure, or electrically decoupling the ECG monitor 210 from the catheter 250 entirely; either way protecting the ECG monitor 210 from damage associated with the high energy defibrillation pulse.

As discussed in reference to FIG. 1, the embodiment of FIG. 2 may also utilize a switch matrix 215 including switches for both controlling the flow of defibrillation pulses to the electrodes 251 and to the ECG monitor (which is otherwise accomplished by the ECG monitor switch 230). By controlling the ECG monitor switch 230 with the impulse detector circuitry 220, an electrical path to the ECG monitor may be decoupled simultaneously to another switch 216 of the switch matrix 215 permitting the defibrillation impulse beyond the switch matrix. This may be particularly beneficial where the ECG monitor switch 230 has a delay between identifying a defibrillation pulse and activating a high impedance state. This also reduces the required circuitry needed.

Charge collector circuitry 222 of FIG. 2 may store energy from a defibrillation pulse, which has been redirected via the impulse detector circuitry 220, for powering driver circuitry 225 for the entirety of a monophasic or bi-phasic waveform of the defibrillation pulse. In some embodiments, as discussed above, the energy storage may be immediately used to power the driver circuitry 225 to maintain a switch matrix in a closed or low impedance state which directs the defibrillation pulse to electrodes 251 of catheter 250 for the duration of the defibrillation pulse. However, the charge time of the charge collector circuitry 222 may cause a time delay between the impulse detector circuitry 220 sensing the defibrillation pulse and the driver circuitry 225 activating the switch matrix 215. Accordingly, various aspects of the present disclosure are directed to storing energy from previous defibrillation pulses for use in later pulses, thereby reducing the delay between sensing the defibrillation pulses and activating the switch matrix 215. In some embodiments, the charge collector 222 may include one or more capacitors that store energy captured from defibrillation pulses. The stored energy may be used to power an impulse detector 220 between defibrillation pulses, and in response to a wake-up signal from the impulse detector, the charge collector may transmit an electrical signal to the driver 225 indicative of the presence of a defibrillation pulse (as sensed by the impulse detector 220). Using the charge from the charge collector, the driver circuitry 225 powers the switch matrix 215 using the remaining stored energy from the previous defibrillation pulse. The presently sensed defibrillation pulse replenishes the capacitor storage within the charge collector 222, and powers the impulse detector circuitry 220 and driver circuitry 225 until the next defibrillation pulse is received. Where the length of time between defibrillation pulses is greater than the capacitor storage can support, the circuitry powers down. As in previous embodiments, the impulse detector 220 may detect the defibrillation pulse and use energy from the defibrillation pulse to power the charge collector circuitry 222. The charge collector 222 stores energy from the defibrillation pulse, which has been redirected via the impulse detector 220, for powering driver circuitry 225 for the entirety of a defibrillation pulse. The driver circuitry 225 regulates the stored energy from the charge collector and provides the necessary drive voltage to activate the switch matrix 215 for the duration of the defibrillation pulse, after which the switch matrix returns to its normally open or high impedance state. The charge collector 222 powering the impulse detector circuitry 220, and driver circuitry 225 until the next defibrillation pulse is received.

Figure 3:
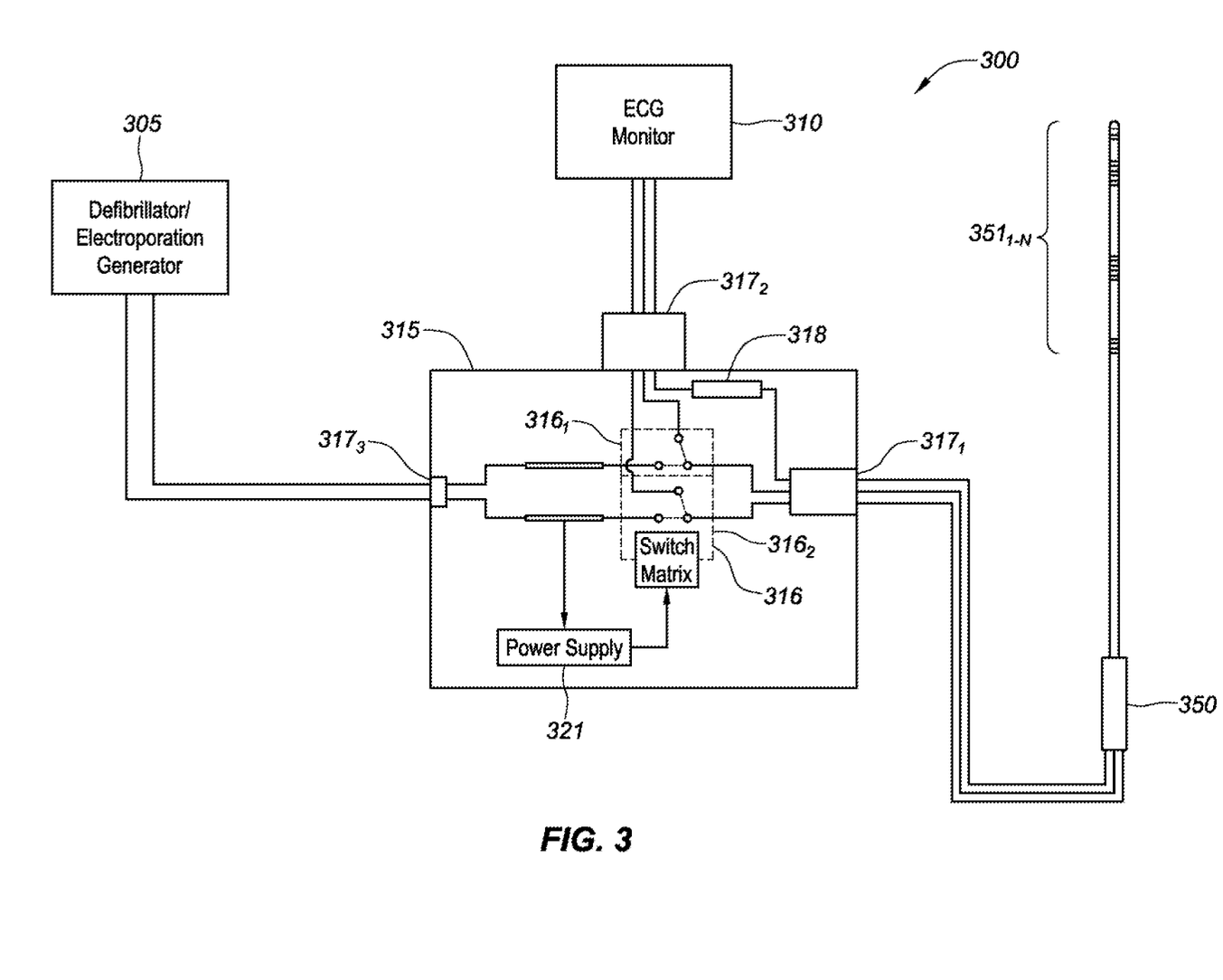
FIG. 3 is a block diagram of an unpowered electronic switchbox, defibrillator/electroporation generator, ECG monitor, and catheter in a diagnostic/therapy catheter system, consistent with various aspects of the present disclosure.

FIG. 3 is a block diagram of a diagnostic/therapy catheter system 300 including a powered electronic switchbox 315, defibrillator/electroporation generator 305, ECG Monitor 310, and catheter 350, consistent with various aspects of the present disclosure.

As shown in FIG. 3, switch matrices $316_{1-2}$ of switch matrix 316 have at least two positions. In the first position, the switch matrices are in a normally open (unpowered) position which connects the ECG monitor 310 to the catheter 350 (via monitor output port $317_2$ of switchbox 315). In position two, a closed (powered) position, the defibrillator 305 is electrically coupled to the catheter 350 and monitor 310 is disconnected (or is placed into a high impedance state to limit the energy received from the generator signal).

With switch matrix 316 in the closed position, a number of electrodes 351 of catheter 350 are electrically decoupled from ECG monitor 310, while those electrodes are electrically coupled to the generator 305 during a defibrillation/electroporation pulse. However, during such a mode, at least one electrode 351 continues to be electrically coupled to the ECG monitor 310 via a filter 318, and thereby continues to monitor tissue in contact with the catheter electrodes. The filter 318 allows the ECG monitor 310 to continue to monitor the tissue while an impulse is delivered to the tissue, while protecting the ECG monitor 310 from the impulse.

Where the generator 305 is a defibrillator, the defibrillator impulse results in cardioversion of tissue in contact with electrodes 351 of the catheter 350. Where the generator is an electroporation generator, the generator produces a direct current that results in ablation of tissue in contact with the electrodes 351 of the catheter 350.

A power supply 321 receives an impulse from a generator 305 via an input port $317_3$ of switchbox 315. When the impulse is first received, switch matrices $316_{1-2}$ of switch matrix 316 are in an open position which prevents the impulse from traveling to electrodes 351 of catheter 350. Power supply 321 energizes a capacitor until reaching a desired threshold voltage, which releases the charge to activate a mode change in the switch matrices $316_{1-2}$ of switch matrix 316—moving the switch matrices into a closed position that electrically couples the generator 305 to one or more catheter electrodes 351. Once the impulse from generator 305 ends, the power supply 321 de-energizes and the switch matrices $316_{1-2}$ of switch matrix 316 revert to an open position. Accordingly, the power supply, in response to an impulse from the generator, switches from a diagnostic mode, to a cardioversion (defibrillation) mode, back to the diagnostic mode.

In one example use of the system as shown in FIG. 3, once power supply circuitry 321 detects an impulse from the generator 305, the power supply system will command (or otherwise power) the switch matrix 316 to a closed position (position 2)—connecting the defibrillator to the catheter for the duration of the impulse (via a switchbox output port $317_1$). Once the defibrillator impulse stops, the switches of the switch matrix will revert to an open position (position 1), allowing ECG recording signals to be restored immediately after the cardioversion therapy has stopped.

In various embodiments, the impulse detection circuitry (as discussed above in reference to FIGS. 1 and 2) and switch matrix 316 may be placed inside the unpowered electronic switchbox 315, which will connect both the ECG monitor 310 and generator 305 to catheter 350. In some specific embodiments, the impulse detection circuitry may be integral to power supply circuitry 321.

As discussed above, a number of electrodes $351_{1-N}$ may be used exclusively for delivering ECG signals to the ECG monitor 310 (e.g., mapping electrodes), without being subjected to cardioversion impulses from generator 305. The ECG signals from the electrodes 351 enter the switchbox 315 but bypass the switch matrix 316. To further protect the ECG monitor 310 from generator impulses, the ECG signals are passed through an impulse protector filter 318. The remaining electrodes 351 (e.g., wide-band electrodes only) both transmit ECG signals and the cardioversion impulses through the switchbox 315 (including the switch matrix 316). In yet more specific embodiments, the switch matrix 316 may include switch matrices for each electrode 351, allowing for each electrode to be independently addressable (to conduct therapy or diagnostics).

Figure 4:
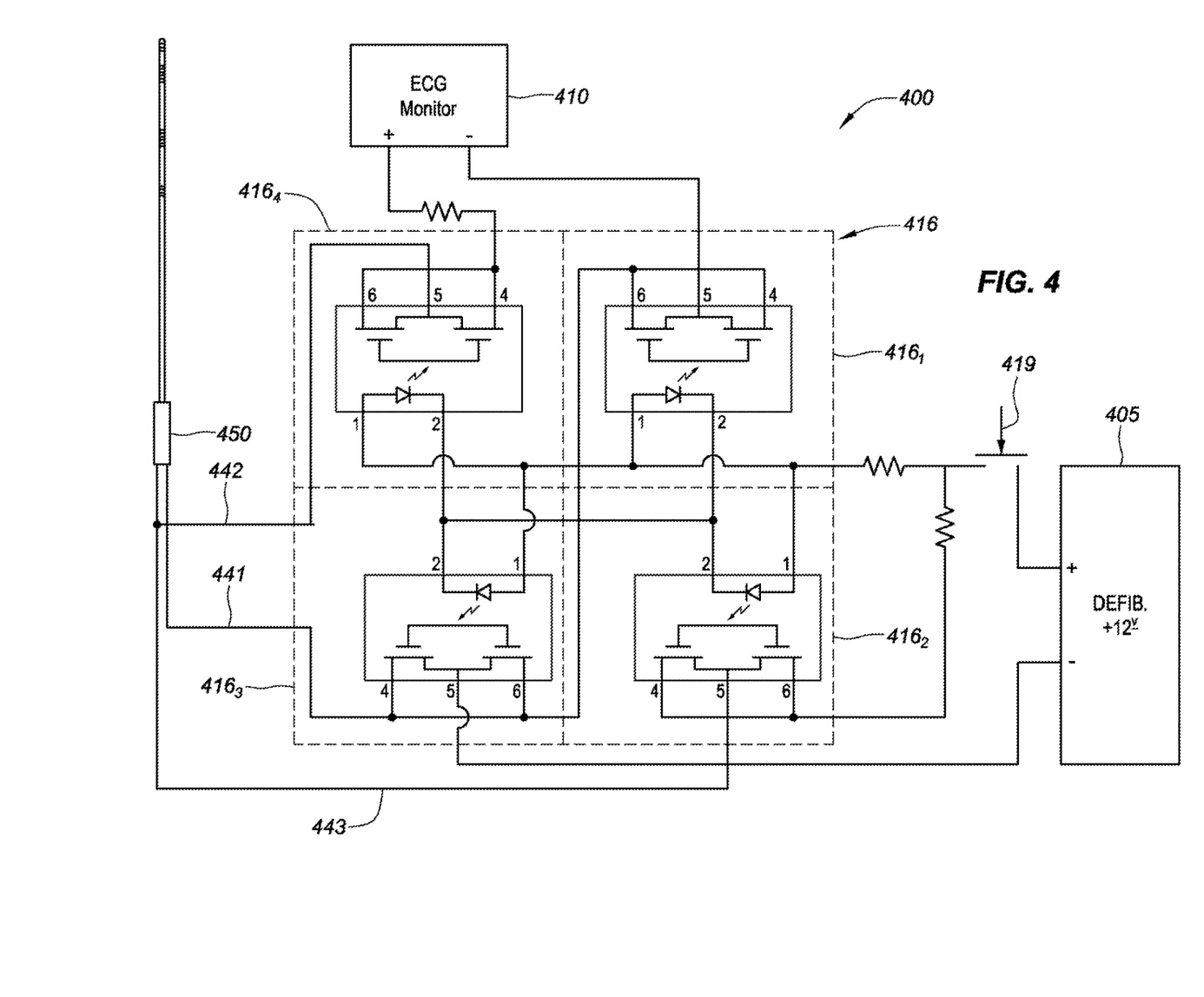
FIG. 4 is a circuit diagram of an unpowered switch matrix electrically coupled between a defibrillator, electrocardiograph monitor, and a diagnostic/therapy catheter, consistent with various aspects of the present disclosure.

FIG. 4 is a circuit diagram of a diagnostic/therapy catheter system 400 including an unpowered electronic switch matrix including switches $416_{1-4}$, the switch matrix electrically coupled between a defibrillator 405, a diagnostic/therapy catheter 450, and an ECG monitor 410, consistent with various aspects of the present disclosure.

In a diagnostic monitoring mode, defibrillator 405 is electrically disconnected from switch matrix 416 by switch 419. When in the diagnostic mode, switches $416_1$ and $416_4$ are in a closed/conducting state (lines 5 and 6 are coupled) which allows a signal and return wires from the ECG monitor 410 to be electrically coupled to signal and return electrodes on catheter 450 via lead wires 442 and 441, respectively. The closed/conducting state of switches $416_1$ and $416_4$ are responsive to the lack of a voltage signal across a diode between lines 1 and 2 of the switches $416_1$ and $416_4$—due to the defibrillator 405 being disconnected from the circuit by switch 419. In the diagnostic monitoring mode, both switches $416_{2-3}$ are in an open/non-conducting state and neither the return or signal wires from the defibrillator 405 are electrically coupled to the catheter 450. As a result, the circuit 400 allows the catheter system to operate in a diagnostic mode where ECG signals from catheter electrodes are delivered to ECG monitor 410.

In a cardioversion mode, defibrillator 405 is electrically connected to switch matrix 416 by switch 419. When in the cardioversion mode, switches $416_1$ and $416_4$ are in an open/non-conducting state (lines 5 and 6 are decoupled) which prevents the signal and return wires from the ECG monitor 410 from electrically coupling to the signal and return electrodes on catheter 450 via lead wires 442 and 441, respectively. The open/non-conducting state of switches $416_1$ and $416_4$ being in response to a voltage across a diode between lines 1 and 2 of the switches $416_1$ and $416_4$—due to the defibrillator 405 electrically coupled via switch 419 to switches $416_{1-4}$. In the cardioversion mode, both switches $416_{2-3}$ are in a closed configuration, electrically coupling the signal and return wires from the defibrillator 405 to lead wires 441 and 443 of the catheter 450 via switches $416_2$ and $416_3$ which are in a closed/conducting state (lines 4 and 5 are coupled. As a result, the catheter system 400 may operate in a cardioversion mode where defibrillation pulses may be delivered to electrodes on the catheter 450, while electrically isolating the ECG monitor 410 from such pulses.

Figure 5:
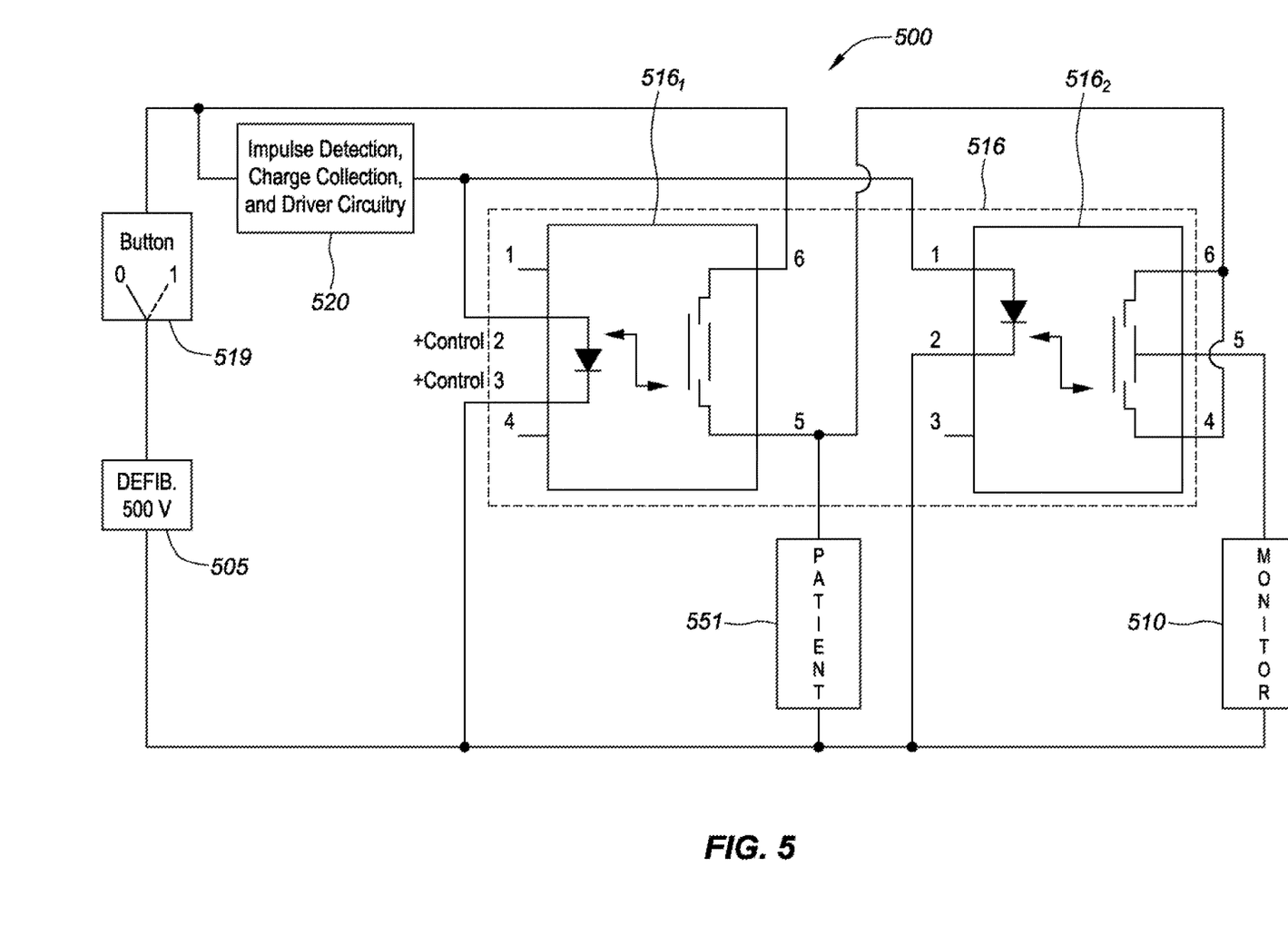
FIG. 5 is a circuit diagram of an unpowered switch matrix electrically coupled between an electrocardiograph monitor, a patient, and a defibrillator, consistent with various aspects of the present disclosure.

FIG. 5 is a circuit diagram 500 of an unpowered electronic switchbox electrically coupled between an electrocardiograph monitor 510, a patient 551, and a defibrillator 505, consistent with various aspects of the present disclosure.

In one example embodiment, a clinician wishes to apply a cardioversion therapy to a patient 551. To apply the desired therapy via the circuit 500 of FIG. 5, a defibrillator signal must travel from the defibrillator 505 through the switch $516_1$ of switch matrix 516 to the patient 551. To accomplish this, switch $516_2$ which electrically couples the patient 551 to monitor 510 must be switched to an open/non-conducting state to prevent the flow of the defibrillation impulse into an input of monitor 510—this is accomplished by having switch $516_1$ in a normally open/non-conducting state and switch $516_2$ in a normally closed/conducting state. In response to the defibrillation impulse, the impulse detection, charge collection, and driver circuitry 520 activate switches $516_1$ and $516_2$ changing the switch states to closed/conducting and open/non- conducting, respectively, which isolates the monitor 510 and directs the defibrillation impulse into patient 551. In various embodiments consistent with the present disclosure, a button/switch 519 may be placed between the defibrillator 505 and switch circuitry 516 to isolate the patient from inadvertent defibrillation pulses, in which case the switch 519 must be placed in the closed position to enable the cardioversion therapy. In many internal cardioversion therapies, the defibrillation impulse may be as high as 30 joules.

The circuitry 500 of FIG. 5 may be duplicated for each electrode channel of a catheter system. That is, each of the electrodes on the catheter tip may have a dedicated circuit 500, which enables each of the electrodes to be independently addressable for tailored therapy applications, as well as simultaneous therapy and diagnostic modes at different electrodes. Based on an electrophysiological mapping of tissue in contact with the various electrodes of the catheter, one or more electrodes may be driven simultaneously to administer a cardioversion therapy at a tissue site. For example, where myocardial tissue in a cardiac muscle is forming a conductive pathway for electrical signals traveling through the tissue, such as in patients suffering from atrial fibrillation, one or more electrodes may be driven simultaneously to ablate the tissue. The cardioversion therapy electrically isolates the sources of such unwanted electrical impulses from the cardiac muscles. One source of such electrical impulses is from arrhythmiatic foci located in the pulmonary veins. By isolating these electrical impulses from the cardiac muscle via cardioversion therapy, which ablates tissue in contact with the electrodes, symptoms relating to atrial fibrillation may be relieved.

Figure 6:
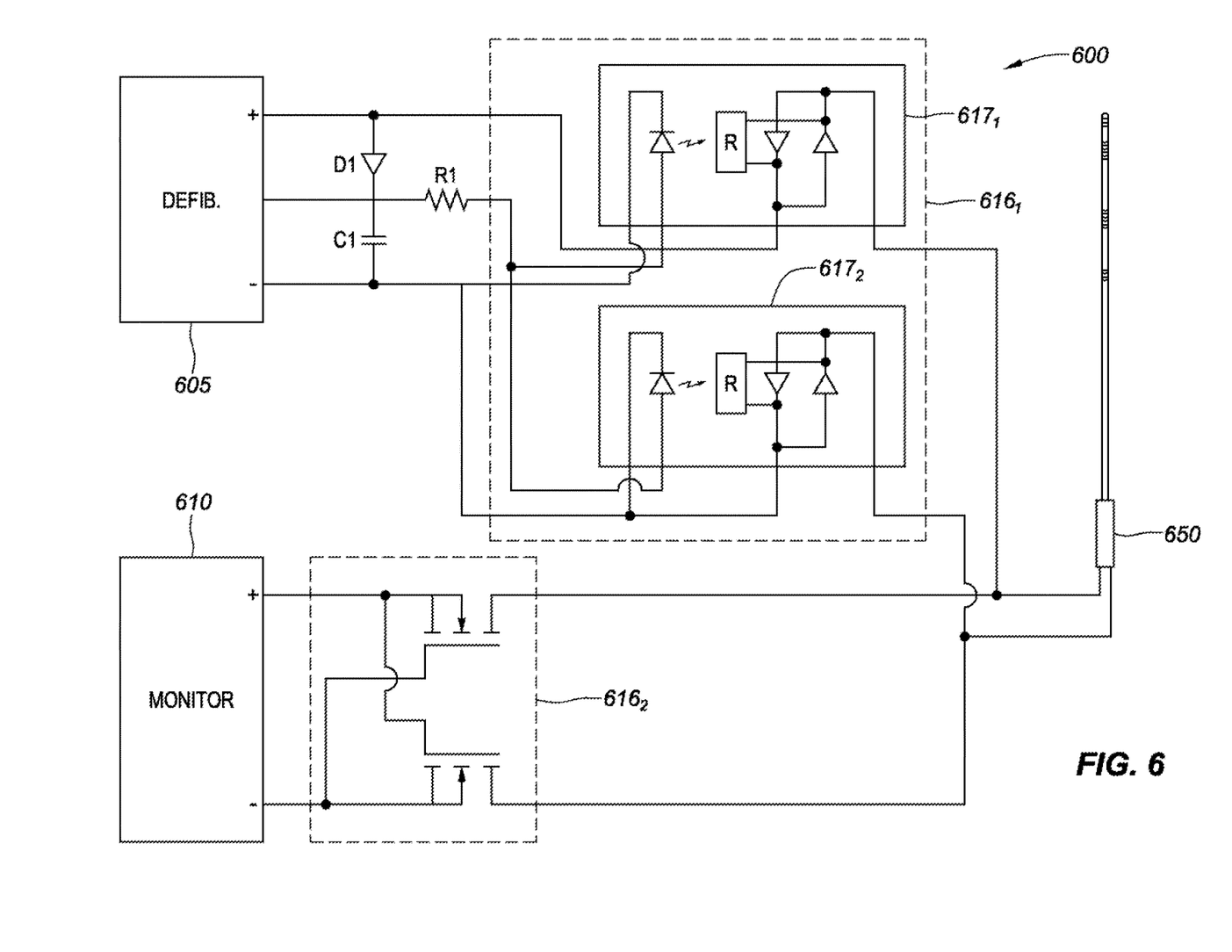
FIG. 6 is a circuit diagram of an unpowered switch matrix electrically coupled between an electrocardiograph monitor, a catheter with electrodes, and a defibrillator, consistent with various aspects of the present disclosure.

FIG. 6 is a circuit diagram 600 of an unpowered electronic switch matrix (including switch matrix portions $616_{1-2}$) electrically coupled between an electrocardiograph monitor 610, a catheter 650 with electrodes, and a defibrillator 605, consistent with various aspects of the present disclosure.

First switch matrix portion $616_1$ includes semiconductor switches $617_{1-2}$ which each individually electrically couple one of a return and signal line from defibrillator 605 to electrodes of catheter 650 in response to a defibrillation impulse. When there is no defibrillation impulse generated by the defibrillator 605, the semiconductor switches $617_{1-2}$ are in an open/non- conducting state, electrically isolating the defibrillator 605 from the electrodes of the catheter 650 and the monitor 610.

When a defibrillation impulse is generated by defibrillator 605, the semiconductor switches $617_{1-2}$ are placed into a closed/conducting state, the defibrillation pulse from the defibrillator 605 travels to the catheter 650. A second semiconductor switch matrix portion $616_2$, in response to the defibrillation impulse, is activated into an open/non-conducting state which electrically isolates the defibrillation impulse from the monitor 610.

In some embodiments consistent with the circuitry 600 of FIG. 6, second semiconductor switch matrix portion $616_2$, in response to the defibrillation impulse, maintains an electrical connection between monitor 610 and catheter 650, but operates in a high-impedance mode that protects the monitor 610 from the defibrillation impulse while allowing the monitor 610 to receive ECG signals during the cardioversion therapy.

As in FIG. 5, the circuitry 600 of FIG. 6 may be duplicated for each electrode channel in the system. To facilitate multiple channel monitoring and therapy application, for each electrode on catheter 650 that both functions as a diagnostic and therapeutic electrode, each electrode may have dedicated first switch matrix portion $616_1$ including semiconductor switches $617_{1-2}$, and a second semiconductor switch matrix portion $616_2$. In such a configuration, each of the electrodes may be independently addressable by the defibrillator 605 to allow for customizable cardioversion treatments while simultaneously allowing each electrode to still communicate ECG signals to monitor 610 for diagnostics—in either a high or low impedance state depending on whether the electrode is receiving a defibrillation impulse.

Based on an electrophysiological mapping of tissue in contact with the various electrodes of the catheter, one or more electrodes may be driven simultaneously to administer a cardioversion therapy at a tissue site. The cardioversion therapy electrically isolates the sources of such unwanted electrical impulses from the cardiac muscles.

Cardioversion is a medical procedure done to restore a normal heart rhythm for patients who have certain types of abnormal heartbeats (e.g., arrhythmias). Cardioversion may be accomplished by sending electric shocks to your heart through electrodes placed on the patient's chest. Cardiac ablation is a procedure that can correct heart rhythm problems (e.g., arrhythmias). Cardiac ablation may create scarring or destroy tissue in a patient's heart that otherwise triggers an abnormal heart rhythm. In some cases, ablation prevents abnormal electrical signals from traveling through the patient's heart, thus stopping the arrhythmia.

Figure 7:
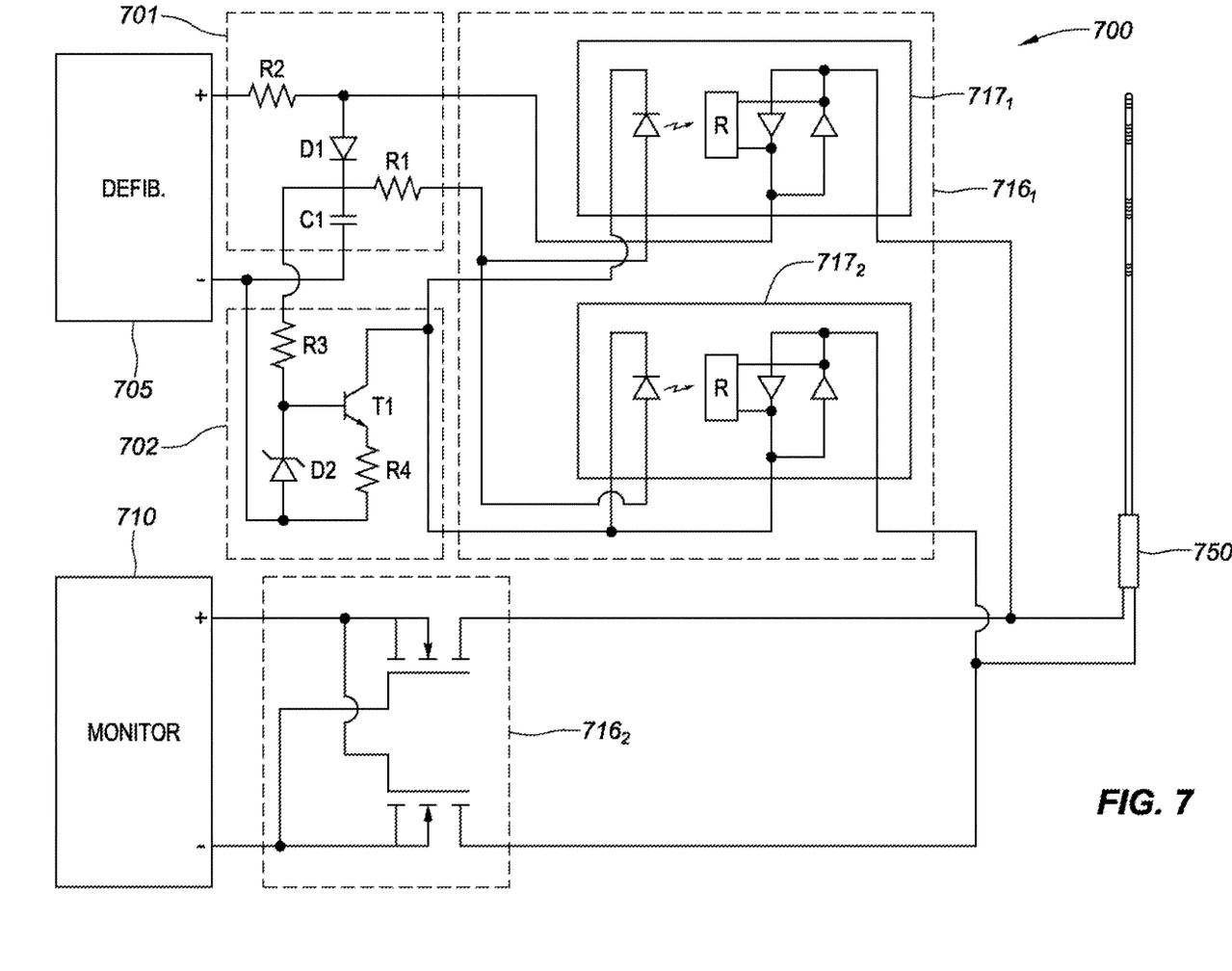
FIG. 7 is a circuit diagram of an unpowered switch matrix electrically coupled between an electrocardiograph monitor, a catheter with electrodes, and a defibrillator, consistent with various aspects of the present disclosure.

FIG. 7 is a circuit diagram 700 of an unpowered electronic switch matrix (including switch matrix portions $716_{1-2}$) electrically coupled between an electrocardiograph monitor 710, a catheter 750 with electrodes, and a defibrillator 705, consistent with various aspects of the present disclosure.

First switch matrix portion $716_1$ includes semiconductor switches $717_{1-2}$ which each individually electrically couple one of a return and signal line from defibrillator 705 to electrodes of catheter 750 in response to a defibrillation impulse. When there is no defibrillation impulse generated by the defibrillator 705, the semiconductor switches $717_{1-2}$ are in an open/non- conducting state, electrically isolating the defibrillator 705 from the electrodes of the catheter 750 and the monitor 710.

When a defibrillation impulse is generated by defibrillator 705, the semiconductor switches $717_{1-2}$ are placed into a closed/conducting state, the defibrillation pulse from the defibrillator 705 travels to the catheter 750. A second semiconductor switch matrix portion $716_2$, which in response to the defibrillation impulse, is activated into an open/non-conducting state which electrically isolates the defibrillation impulse from the monitor 710.

In some embodiments consistent with circuitry 700 of FIG. 6, second semiconductor switch matrix portion $716_2$, in response to the defibrillation impulse, maintains an electrical connection between monitor 710 and catheter 750, but in a high-impedance mode that protects the monitor 710 from the defibrillation impulse while allowing the monitor 710 to receive ECG signals during the cardioversion therapy.

As in FIGS. 5 and 6, the circuitry 700 of FIG. 7 may be duplicated for each electrode channel in the system. To facilitate multiple channel monitoring and therapy application, for each electrode on catheter 750 that both functions as a diagnostic and therapeutic electrode, each electrode may have dedicated first switch matrix portion $716_1$ including semiconductor switches $717_{1-2}$, and a second semiconductor switch matrix portion $716_2$. In such a configuration, each of the electrodes may be independently addressable by the defibrillator 705 to allow for customizable cardioversion treatments while simultaneously allowing each electrode to still communicate ECG signals to monitor 710 for diagnostics—in either a high or low impedance state depending on whether the electrode is receiving a defibrillation impulse.

The circuit diagram 700 further includes an impulse detection and charge storage sub-circuit 701. The impulse detection and charge storage sub-circuit 701 includes resistor R2, diode D1, and capacitor C1 components which function as in impulse detecting circuit by integrating the positive pulse of the defibrillation signal. A level of integration is set by the value of R2 and C1, and used to prevent false triggering due to noise on the signal lines. The D1 and C1 components also function as the charge storage elements of the impulse detection and charge storage sub-circuit 701—where C1 is charged during the positive portion of the defibrillation cycle and is used to maintain power to the switch matrix during the negative portion of the defibrillation cycle. The amount of charge that is stored is dependent on the magnitude and duration of the positive defibrillation pulse as well as the level of integration which is set by R2 and C1. R1 in this circuit is just a current limiter for switch matrix drive circuit 702, as described in more detail below.

The circuit diagram 700 also includes a switch matrix drive circuit 702. The switch matrix drive circuit 702 includes two resistors, R3 and R4, diode D2 (which in some embodiments may be a Zener diode), and a transistor T1. The switch matrix drive circuit 702 produces a constant current (current source) for an opto-isolated control circuit in switch elements $717_{1-2}$. The switch matrix drive circuit 702 also keeps the switch matrix $716_1$ in the closed/conducting (active) state until the stored charge in C1 is depleted to a point where the switch matrix $716_1$ cannot be maintained in the active state. The duration the switch matrix $716_1$ is maintained in the active state is a function of the charge stored in C1, the drive current which is set by R2, and the number of switch elements in the switch matrix $716_1$.

An impulse detection and charge storage sub-circuit 701 and a switch matrix drive circuit 702 as disclosed in FIG. 7 may further be used to drive other types of switches that are controlled through current sources or the circuit(s) can be modified to be a voltage source to drive switches that are controlled via voltage sources.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Based upon the above discussion and illustrations, those skilled in the art will readily recognize that various modifications and changes may be made to the various embodiments without strictly following the exemplary embodiments and applications illustrated and described herein. For example, the various electronics components presented in the various circuit diagrams may be replaced with one or more components capable of replicating the functionality, and/or the processing order may be interchanged. Such modifications do not depart from the true spirit and scope of various aspects of the invention, including aspects set forth in the claims.

Various modules or other circuits may be implemented to carry out one or more of the operations and activities described herein and/or shown in the figures. In these contexts, a "module" is a circuit that carries out one or more of these or related operations/activities (e.g., a switch matrix). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electronic switchbox comprising:
   impulse detection circuitry configured and arranged to detect a pulse emitted from a signal generator; and
   a switch matrix including one or more switches, the switch matrix configured and arranged to operate in:
      a first mode whereby the pulse is electrically isolated from an electrocardiograph monitor and a plurality of catheter electrodes, and
      in response to an activation signal from the impulse detection circuitry indicative of the pulse, a second mode whereby the pulse is electrically coupled to at least one of the plurality of catheter electrodes, and a high impedance state protects the electrocardiograph monitor from the pulse;
   wherein the switch matrix is further configured and arranged to facilitate communication of electrocardiograph signals to the electrocardiograph monitor during both the first and second modes using identical catheter electrodes of the plurality of catheter electrodes.

2. The electronic switchbox of claim 1, further including driver circuitry configured and arranged to operate the switch matrix in the first and second modes in response to a trigger signal from the impulse detection circuitry;
   wherein the impulse detection circuitry is further configured and arranged to receive the pulse emitted from the signal generator and use a portion of the energy from the pulse to power the impulse detection circuitry, generate the trigger signal and deliver the trigger signal to the driver circuitry; and
   wherein the pulse emitted by the signal generator is at least one of a cardioversion pulse or a direct current electroporation pulse.

3. The electronic switchbox of claim 2, further including charge collector circuitry electrically coupled between the driver circuitry and the impulse detection circuitry, the charge collector circuitry configured and arranged to store energy from the pulse and power the driver circuitry during the pulse.

4. The electronic switchbox of claim 2, further including power supply circuitry configured and arranged to power the driver circuitry during the pulse.

5. The electronic switchbox of claim 1, wherein the switch matrix is further configured and arranged to facilitate automatic transitions between the first and second modes without clinician intervention, and wherein the first mode is associated with electrophysiological diagnostics of tissue, and the second mode is associated with cardioversion therapy of the tissue.

6. The electronic switchbox of claim 1, wherein the switch matrix is further configured and arranged to facilitate electrophysiological diagnostics during both the first and second modes.

7. The electronic switchbox of claim 1, wherein the switch matrix further includes an electrocardiograph monitor switch, which in response to the second mode is configured and arranged to enter a high impedance state that protects the electrocardiograph monitor from the pulse.

8. The electronic switchbox of claim 1, further including a plurality of electrode channels electrically coupled between the switch matrix and the plurality of catheter electrodes, the plurality of electrode channels, in conjunction with the switch matrix, are configured and arranged to be independently addressable to facilitate a plurality of electrophysiological diagnostic and cardioversion therapy configurations.

9. The electronic switchbox of claim 8, wherein the plurality of catheter electrodes, the plurality of electrode channels, and the switch matrix are configured and arranged to facilitate simultaneous electrophysiological diagnostics and cardioversion therapy.

10. The electronic switchbox of claim 1, wherein the pulse emitted by the signal generator is at least one of a cardioversion pulse, or a direct current electroporation pulse.

11. A cardiovascular catheter system comprising:
    a signal generator configured and arranged to generate an electrical pulse for cardioverting or ablating tissue;
    an electrocardiograph monitor configured and arranged to receive and monitor electrocardiograph signals indicative of the electrical activity of a heart;
    a cardiac catheter including a plurality of electrodes along a length of a distal portion, the plurality of electrodes configured and arranged to electrically couple to the tissue and cardiovert or ablate the tissue in response to the electrical pulse;
    an electronic switch box including:
       impulse detection circuitry electrically coupled to the signal generator and configured and arranged to detect the electrical pulse emitted from the signal generator, and
       a switch matrix including one or more switches, an input port, and an output port, the switch matrix electrically coupled to the impulse detection circuitry and the signal generator at the input port, and the plurality of electrodes and the electrocardiograph monitor at the output port, the switch matrix configured and arranged to operate in:
          a first mode whereby the electrical pulse is isolated from the electrocardiograph monitor and the plurality of catheter electrodes, and
          a second mode, in response to an activation signal from the impulse detection circuitry indicative of the electrical pulse, whereby the electrical pulse is electrically coupled to at least one of the plurality of catheter electrodes, and a high impedance state protects the electrocardiograph monitor from the electrical pulse;

wherein the switch matrix is further configured and arranged to facilitate the communication of electrocardiograph signals to the electrocardiograph monitor during both the first and second modes using identical catheter electrodes of the plurality of catheter electrodes.

12. The cardiovascular catheter system of claim 11, wherein the electrical pulse generated by the signal generator is at least one of a cardioversion pulse, or a direct current electroporation pulse.

13. The cardiovascular catheter system of claim 11, wherein the electronic switch box further includes driver circuitry configured and arranged to change the switch matrix between the first and second modes in response to a trigger signal from the impulse detection circuitry; and wherein the impulse detection circuitry is further configured and arranged to use energy from the electrical pulse to deliver the trigger signal to the driver circuitry.

14. The cardiovascular catheter system of claim 13, wherein the electronic switch box further includes charge collector circuitry electrically coupled between the driver circuitry and the impulse detection circuitry, the charge collector circuitry configured and arranged to store energy from the electrical pulse and power the driver circuitry.

15. A method of operating an electronic switch box comprising:

in the absence of an electrical pulse, operating in a first mode whereby an input port of the switch box is isolated from an electrocardiograph monitor and a plurality of catheter electrodes electrically coupled to an output port of the switch box, and operating in a second mode, in response to the electrical pulse, whereby the input port receiving the electrical pulse is electrically coupled to at least one of the plurality of catheter electrodes, and the electrocardiograph monitor via the output port of the switch box, and the electrocardiograph monitor is protected from the electrical pulse by a high impedance between the output port of the switch box and the electrocardiograph monitor;

wherein electrocardiograph signals from identical catheter electrodes of the plurality of catheter electrodes are communicatively coupled to the electrocardiograph monitor during both the first and second modes.

16. The method of operating the electronic switch box of claim 15, wherein charge collector circuitry stores energy from the electrical pulse and maintains the switch box in the second mode during the electrical pulse.

* * * * *

UNITED STATES PATENT AND TRADEMARK OFFICE
CERTIFICATE OF CORRECTION

| | | |
|---|---|---|
| PATENT NO. | : 11,446,082 B2 | Page 1 of 1 |
| APPLICATION NO. | : 15/878522 | |
| DATED | : September 20, 2022 | |
| INVENTOR(S) | : Blanck et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1277 days.

Signed and Sealed this
Fourth Day of February, 2025

Coke Morgan Stewart
*Acting Director of the United States Patent and Trademark Office*